United States Patent [19]
Igari et al.

[11] Patent Number: 6,045,830
[45] Date of Patent: Apr. 4, 2000

[54] METHOD OF PRODUCTION OF SUSTAINED-RELEASE PREPARATION

[75] Inventors: Yasutaka Igari; Shigeyuki Takada, both of Hyogo; Hiroshi Kosakai, Kanagawa, all of Japan

[73] Assignee: Takeda Chemical Industries, Ltd., Osaka, Japan

[21] Appl. No.: 08/704,991

[22] Filed: Aug. 29, 1996

[30] Foreign Application Priority Data

Sep. 4, 1995 [JP] Japan ................................. 7-226457

[51] Int. Cl.$^7$ .............................. A61K 9/16; A61K 47/34
[52] U.S. Cl. ...................... 424/501; 424/426; 428/402.24
[58] Field of Search ................................. 424/426, 428, 424/486, 501; 525/450; 428/402, 402.24; 514/772.7

[56] References Cited

FOREIGN PATENT DOCUMENTS

| | | |
|---|---|---|
| 0 145 240 | 6/1985 | European Pat. Off. . |
| 0 178 824 | 4/1986 | European Pat. Off. . |
| 0 442 671 | 8/1991 | European Pat. Off. . |
| 0 586 238 | 3/1994 | European Pat. Off. . |
| 4-217914 | 8/1992 | Japan . |
| 2 246 514 | 2/1992 | United Kingdom . |
| 89/04673 | 6/1989 | WIPO . |
| 96/07399 | 3/1996 | WIPO . |

OTHER PUBLICATIONS

Keipert et al., "Antiglaumakotosaaltige Ophthalmika Mit Prolongierter Wirkung Aug Basis Makromolekularer Hilfsstoffe", Die Pharmazie, vol. 45, No. 8, (1990), pp. 594–595.

*Primary Examiner*—Edward J. Webman
*Attorney, Agent, or Firm*—Foley & Lardner

[57] ABSTRACT

A method of production of sustained-release microcapsules that comprises obtaining microcapsules comprising a bioactive substance that are encapsulated with a biodegradable polymer, and thermally drying the obtained microcapsules at a temperature not lower than the glass transition temperature of the biodegradable polymer for about 24 to about 120 hours to produce the sustained-release microcapsules comprising, relative to the weight of the sustained-release microcapsule, not less than 60% (w/w) of the biodegradable polymer, possessing pharmaceutical characteristics clinically excellent in that a bioactive substance is released at constant rate over a very long period of time from just after administration with dramatically suppressed initial release of the bioactive substance in excess just after administration and with minimum remaining organic solvent.

16 Claims, No Drawings

METHOD OF PRODUCTION OF SUSTAINED-RELEASE PREPARATION

FIELD OF THE INVENTION

The present invention relates mainly to a method of producing sustained-release microcapsules that release a bioactive substance at constant rate over an extended period of time from just after administration with suppressed initial release of the bioactive substance in excess just after administration.

BACKGROUND OF THE INVENTION

PCT International publication No. WO89/04673 [Tokuhyo (Publication of the Translation of International Patent Application) 503315/1990] discloses a method of producing a solid polymer preparation wherein said solid preparation is kept at a temperature not lower than the glass transition point of the constituent polymer.

EPA No. 0586238 discloses a method of producing sustained-release microcapsules containing a biologically active substance from an W/O emulsion comprising an inner aqueous phase containing said biologically active substance and an external oil phase containing a biodegradable polymer, characterized in that microcapsules formed on microencapsulation of said biologically active substance with said biodegradable polymer heated at a temperature not lower than the glass transition temperature of said biodegradable polymer but not so high as to cause aggregation of the microcapsules.

With regard to sustained-release microcapsules incorporating a biodegradable polymer, it is desirable that the initial release of the bioactive substance, especially that in excess within 1 day, be suppressed, and that the release of the bioactive substance be optionally controlled over an extended period of time. However, the description in the above-mentioned patent publications does not enable the production of fully satisfactory sustained-release microcapsules that release the bioactive substance, especially polypeptide having a high molecular weight, at constant rate over an extended period of time from just after administration with suppressed initial release of the bioactive substance in excess just after administration.

SUMMARY OF THE INVENTION

Through intensive investigation to resolve the above problems, the present inventors found it possible to produce sustained-release microcapsules containing a bioactive substance and a biodegradable polymer possessing pharmaceutical characteristics clinically excellent in that the bioactive substance is released at constant rate over a very long period of time from just after administration with unexpectedly dramatically suppressed initial release of the bioactive substance in excess just after administration and with minimum retention of organic solvent, by incorporating the biodegradable polymer at not less than 60% (w/w), and heating or thermally drying the microcapsules at a temperature not lower than the glass transition point of said polymer for about 24 to 120 hours. After further investigations based on this finding, the inventors developed the present invention.

(1) A method of production of sustained-release microcapsules that comprises obtaining microcapsules comprising a bioactive substance that are encapsulated with a biodegradable polymer, and thermally drying the obtained microcapsules at a temperature not lower than the glass transition temperature of the biodegradable polymer for about 24 to about 120 hours to produce the sustained-release microcapsules comprising, relative to the weight of the sustained-release microcapsule, not less than 60% (w/w) of the biodegradable polymer.

(2) A method for production of 1, wherein said bioactive substance is a peptide having a molecular weight of about 200 to 20,000.

(3) A method for production of (1), wherein said bioactive substance is luteinizing hormone-releasing hormone or an analog thereof.

(4) A method for production of (1), wherein said bioactive substance is a peptide represented by the formula (I):

$$(Pyr)Glu-R_1-Trp-Ser-R_2-R_3-R_4-Arg-Pro-R_5 \qquad (I)$$

wherein $R_1$ represents His, Tyr, Trp or p-$NH_2$-Phe; $R_2$ represents Tyr or Phe; $R_3$ represents Gly or a D type amino acid residue; $R_4$ represents Leu, Ile or Nle; and $R_5$ represents Gly-NH-$R_6$ ($R_6$ represents a hydrogen atom or a lower alkyl group with or without a hydroxyl group) or NH-$R_6$ ($R_6$ has the same definition as that shown above); or a salt thereof.

(5) A method for production of (1), wherein said bioactive substance is: (Pyr)Glu-His-Trp-Ser-Tyr-D-Leu-Leu-Arg-Pro-$NHCH_2$-$CH_3$ or a salt thereof.

(6) A method for production of (1), wherein said bioactive substance is a peptide represented by the formula (II):

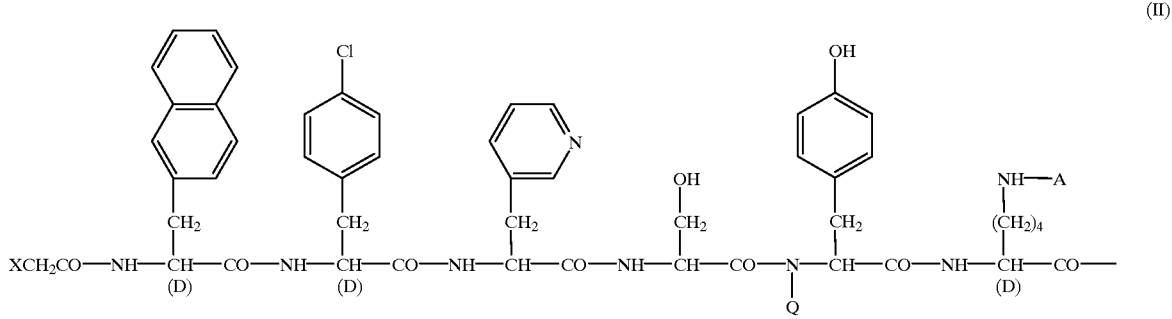

-continued

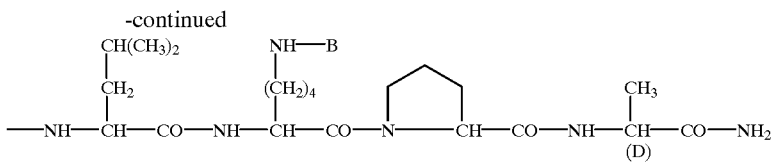

wherein X represents a hydrogen atom or a tetrahydrofurylcarboxamido; Q represents a hydrogen atom or methyl; A represents nicotinoyl or N,N'-diethylamidino; and B represents isopropyl or N,N'-diethylamidino or a salt thereof.

(7) A method for production of (6), wherein X is a tetrahydrofurylcarboxamido.

(8) A method for production of (6), wherein X is (2S)-tetrahydrofurylcarboxamido.

(9) A method for production of (6), wherein X is (2S)-tetrahydrofurylQarboxamido, Q is methyl, A is nicotinoyl, and B is isopropyl.

(10) A method for production of (1), wherein said bioactive substance is thyroid horomone-releasing hormone.

(11) A method for production of (1), wherein the content ratio of said biodegradable polymer is not less than 70% (w/w).

(12) A method for production of (1), wherein said biodegradable polymer is a homopolymer or copolymer of α-hydroxycarboxylic acids or a mixture thereof.

(13) A method for production of (1), wherein said biodegradable polymer is a homopolymer or copolymer of lactic acid/glycolic acid having a lactic acid/glycolic acid ratio of about 100/0 to 50/50 mol %.

(14) A method for production of (1), wherein said biodegradable polymer is a homopolymer of lactic acid.

(15) A method for production of (1), wherein the weight-average molecular weight of said biodegradable polymer is 3,000 to 30,000.

(16) A method for production of (1), wherein microcapsules are thermally dried in a temperature ranging from the glass transition point of said biodegradable polymer to a temperature about 30° C. higher than the glass transition point.

(17) A method for production of (1), wherein microcapsules are thermally dried at a temperature ranging from the glass transition point of said biodegradable polymer to a temperature by 5° C. higher than the glass transition point.

(18) A method for production of (1), wherein microcapsules are thermally dried for about 48 to 120 hours.

(19) A method for production of (1), wherein the microcapsules are obtained by an in-water drying method.

(20) A method for production of (1), wherein the content ratio of the bioactive substance relative to the sustained-release microcapsules is 0.01 to 40% (w/w).

(21) A method for production of (4), wherein the sustained-release microcapsules contain the bioactive substance at the final content ratio of 5–15% (w/w) and the biodegradable polymer at the final content ratio of 80–95% (w/w).

(22) Sustained-release microcapsules obtained by the method for production of (1).

(23) Microcapsules of (22) which is for injection.

(24) An agent for treatment or prevention of sex hormone-dependent diseases or a contraceptive which comprises the sustained-release microcapsules of (22).

(25) An agent of (24), wherein said sex hormone-dependent disease is prostatic hypertrophy, prostatic cancer, hysteromyoma, endometriosis, dysmenorrhea, precocious puberty or breast cancer.

(26) A method for treatment or prevention of sex hormone-dependent diseases in a subject which comprises administering to said subject in need an effective amount of the microcapsules of (22).

(27) Use of the microcapsules of (22) for manufacture of an agent for treatment or prevention of sex hormone-dependent diseases or a contraceptive.

(28) A composition for the treatment or prevention of sex hormone-dependent disease or a contraceptive, made from a microcapsule as claimed in (22).

(29) A method for treating a microcapsule comprising a bioactive substance that is encapsulated with a biodegradable polymer, which comprises thermally drying the microcapsule at a temperature not lower than the glass transition temperature of the biodegradable polymer for about 24 to about 120 hours, wherein the microcapsule comprises the biodegradable polymer at a final content ratio of not less than 60% (w/w).

Abbreviations for amino acids, protecting groups and others used in the present specification are based on abbreviations specified by the IUPAC-IUB Commission on Biochemical Nomenclature or abbreviations in common use in relevant fields. When an optical isomer may be present in amino acid, it is of the L-configuration, unless otherwise stated.

Other abbreviations used in the present specification are defined as follows:

NAcD2Nal: N-acetyl-D-3-(2-naphthyl)alanyl
D4ClPhe: D-3-(4-chlorophenyl)alanyl
D3Pal: D-3-(3-pyridyl)alanyl
NMeTyr: N-methyltyrosyl
DLys(Nic): D-(ipsiron-N-nicotinoyl)lysyl
Lys(Nisp): (Ipsiron-N-isopropyl)lysyl
DhArg(Et2): D-(N,N'-diethyl)homoalginyl

DETAILED DESCRIPTION OF THE INVENTION

Bioactive substances useful for the present invention include, but are not limited to, bioactive peptides, antitumor agents, antibiotics, antipyretic analgesic antiinflammatory agents, antitussive expectorants, sedatives, muscle relaxants, antiepileptics, antiulcer agents, antidepressants, anti-allergic agents, cardiotonics, antiarrhythmic agents, vasodilators, hypotensive diuretics, antidiabetics, anticoagulants, hemolytics, antituberculosis agents, hormones, narcotic antagonists, bone resorption suppressors and angiogenesis suppressors.

The bioactive substance for the present invention is preferably a bioactive peptide. Preferably, said peptide consists of 2 or more amino acids and has a molecular weight of about 200 to 80,000. More preferably about 300 to 40,000. Most preferred bioactive substance is a peptide having a molecular weight of about 1,000 to 20,000.

Such peptides include luteinizing hormone-releasing hormone (LH-RH) and analogues thereof such as LH-RH agonists and LH-RH antagonists. Representative LH-RH agonists include the peptide represented by the formula (I):

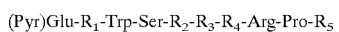

wherein $R_1$ represents His, Tyr, Trp or p-$NH_2$-Phe; $R_2$ represents Tyr or Phe; $R_3$ represents Gly or a D-type amino acid residue; $R_4$ represents Leu, Ile or Nle; $R_5$ represents Gly-NH-$R_6$ ($R_6$ is a hydrogen atom or a lower alkyl group with or without a hydroxyl group) or NH-$R_6$ ($R_6$ has the same definition as that shown above) [hereinafter sometimes referred to briefly as peptide (I)]; or a salt thereof [see U.S. Pat. Nos. 3,853,837, 4,008,209 and 3,972,859, British Patent No. 1,423,083, Proceedings of the National Academy of Science of the United States of America, Vol. 78, pp. 6509–6512 (1981)].

With respect to peptide (I), the D-type amino acid residue represented by $R_3$ is exemplified by α-D-amino acids having up to 9 carbon atoms (e.g., D-Leu, Ile, Nle, Val, Nval, Abu, Phe, Phg, Ser, Thr, Met, Ala, Trp, α-Aibu). These amino acid residues may have a protecting group (e.g., t-butyl, t-butoxy, t-butoxycarbonyl) as appropriate. Acid salts (e.g., carbonate, bicarbonate, acetate, propionate) and metal complex compounds (e.g., copper complex, zinc complex) of peptide (I) can also be used as is peptide (I).

Representative examples of peptide (I) include the peptide wherein $R_1$ is His, $R_2$ is Tyr, $R_3$ is D-Leu, $R_4$ is Leu, and $R_5$ is $NHCH_2$—$CH_3$ (the acetate of this peptide is commonly known as leuprorelin acetate and hereinafter also referred to as TAP-144).

Bioactive peptides include LH-RH antagonists (see U.S. Pat. Nos. 4,086,219, 4,124,577, 4,253,997 and 4,317,815), such as the peptide represented by the formula (II):

With respect to peptide (II), X is preferably a tetrahydrofurylcarboxamido, more preferably (2S)-tetrahydrofurylcarboxamido. Also, A is preferably nicotinoyl; B is preferably isopropyl.

When peptide (II) has one or more kinds of asymmetric carbon atoms, two or more optical isomers are present. Such optical isomers and mixtures thereof are also included in the scope of the present invention.

Peptide (II) or a salt thereof can be produced by per se known methods. Such methods include the methods described in Japanese Patent Unexamined Publication No. 101695/1991 and the Journal of Medicinal Chemistry, Vol. 35, p. 3942 (1992) and other publications, and similar methods.

The salt of peptide (II) is preferably a pharmacologically acceptable salt. Such salts include salts with inorganic acids (e.g., hydrochloric acid, sulfuric acid, nitric acid), organic acids (e.g., carbonic acid, bicarbonic acid, succinic acid, acetic acid, propionic acid, trifluoroacetic acid, pamoic acid) etc. More preferably, the salt of peptide (II) is the salt with an organic acid (e.g., carbonic acid, bicarbonic acid, succinic acid, acetic acid, propionic acid, trifluoroacetic acid, pamoic

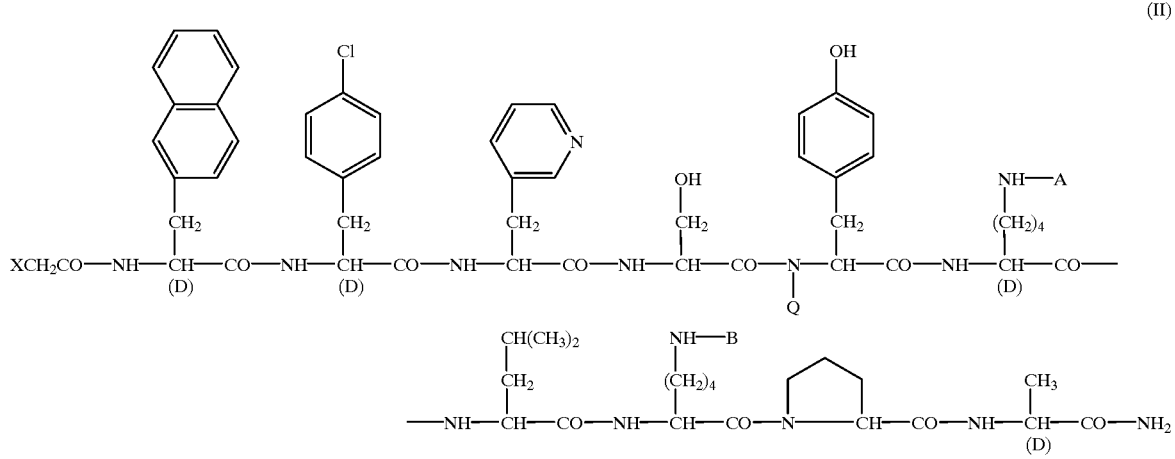

(II)

wherein X represents a hydrogen atom or a tetrahydrofurylcarboxamido; Q represents a hydrogen atom or methyl; A represents nicotinoyl or N,N'-diethylamidino; B represents isopropyl or N,N'-diethylamidino (hereinafter referred to briefly as peptide (II)); or a salt thereof.

acid), with greater preference given to the salt with acetic acid. Although these salts may be mono- through tri-salts, di-through tri-salts are preferred.

Preferable examples of peptide (II) or a salt thereof are given below.

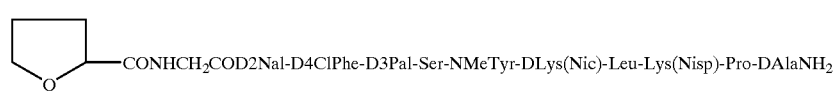

(1)

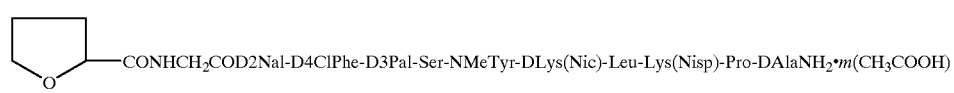

(2)

wherein m represents a real number from 1 to 3.
(3) NAcD2Nal-D4ClPhe-D3Pal-Ser-Tyr-DhArg(Et2)-Leu-hArg(Et2)-Pro-DAlaNH2
(4) NAcD2Nal-D4ClPhe-D3Pal-Ser-Tyr-DhArg(Et2)-Leu-hArg(Et2)-Pro-DAlaNH2.n(CH₃COOH)
wherein n represents a real number from 1 to 3.

Peptide (II) or the salt thereof is preferably (1) or (2) above.

Example of the bioactive peptides include insulin, somatostatin, somatostatin derivatives (see U.S. Pat. Nos. 4,087,390, 4,093,574, 4,100,117 and 4,253,998), growth hormones, prolactin, adrenocorticotropic hormone (ACTH), melanocyte-stimulating hormone (MSH), thyroid hormone-releasing hormone [represented by the structural formula (Pyr)Glu-His-ProNH$_2$, hereinafter also referred to as TRH] and salts and derivatives thereof [see Japanese Patent Unexamined Publication Nos. 121273/1975 (U.S. Pat. No. 3,959,247) and 116465/1977 (U.S. Pat. No. 4,100,152)], thyroid-stimulating hormone (TSH), luteinizing hormone (LH), follicle-stimulating hormone (FSH), vasopressin, vasopressin derivatives [desmopressin, see Folia Endocrinologica Japonica, Vol. 54, No. 5, pp. 676–691 (1978)], oxytocin, calcitonin, parathyroid hormone, glucagon, gastrin, secretin, pancreozymin, cholecystokinin, angiotensin, human placental lactogen, human chorionic gonadotropin (HCG), enkephalin, enkephalin derivatives (see U.S. Pat. No. 4,277,394 and European Patent Publication No. 31567), endorphin, kyotorphin, interferons (e.g., α-, β- and γ-interferons), interleukins (e.g., interleukins I, II and III), tuftsin, thymopoietin, thymosin, thymostimulin, thymic humoral factor (THF), blood thymic factor (FTS) and derivatives thereof (see U.S. Pat. No. 4,229,438), other thymic factors [Igaku no Ayumi, Vol. 125, No. 10, pp. 835–843 (1983)], tumor necrosis factor (TNF), colony-stimulating factor (CSF), motilin, daynorphin, bombesin, neurotensin, caerulein, bradykinin, urokinase, asparaginase, kallikrein, substance P, nerve growth factor, cell growth factor, nerve nutrition factor, hemagglutination factors VIII and IX, lysozyme chloride, polymixin B, colistin, gramicidin, bacitracin, erythropoietin (EPO), and endothelin-antagonistic peptides (see European Patent Publication Nos. 436189, 457195 and 496452, and Japanese Patent Unexamined Publication Nos. 94692/1991 and 130299/1991).

Example antitumor agents include bleomycin, methotrexate, actinomycin D, mitomycin C, vinblastin sulfate, vincrystin sulfate, daunorubicin, adriamycin, neocarzino-statin, cytosinearabinoside, fluorouracil, tetrahydrofuryl-5-fluorouracil, krestin, Picivanil, lentinan, levamisole, Bestatin, glycyrrhizin, polyI:C, polyA:U and polyICLC.

Example antibiotics include gentamicin, dibekacin, Kanendomycin, lividomycin, tobramycin, amikacin, fradiomycin, sisomycin, tetracycline hydrochloride, oxytetra-cycline hydrochloride, rolitetracycline, doxycycline hydrochloride, ampicillin, piperacillin, ticarcillin, cefalothin, cefaloridine, cefotiam, cefsulodin, cefmenoxime, cefmetazole, cefazolin, cefotaxime, cefoperazon, ceftizoxime, mochisalactam, thienamycin, sulfazecin and aztreonam.

Example antipyretic analgesic anti-inflammatory agents include salicylic acid, sulpyrine, flufenamic acid, diclofenac, indomethacin, morphine, pethidine hydrochloride, levorphanol tartrate and oxymorphone.

Example antitussive expectorants include ephedrine hydrochloride, methylephedrine hydrochloride, noscapine hydrochloride, codeine phosphate, dihydrocodeine phosphate, allocramide hydrochloride, clofedanol hydrochloride, picoperidamine hydrochloride, chloperastine, protokylol hydrochloride, isoproterenol hydrochloride, sulbutamol sulfate and terbutaline sulfate.

Example sedatives include chlorpromazine, prochlorperazine, trifluoperazine, atropine sulfate and methylscopolamine bromide.

Example muscle relaxants include pridinol methanesulfonate, tubocurarine chloride and pancuronium bromide.

Example antiepileptics include phenytoin, ethosuximide, acetazolamide sodium and chlordiazepoxide.

Example antiulcer agents include metoclopramide and histidine hydrochloride.

Example antidepressants include imipramine, clomipramine, noxiptiline and phenerdine sulfate.

Example anti-allergic agents include diphenhydramine hydrochloride, chlorpheniramine maleate, tripelenamine hydrochloride, clemizole hydrochloride, diphenylpyraline hydrochloride and methoxyphenamine hydrochloride.

Example cardiotonics include trans-pai-oxocamphor, theophyllol, aminophylline and etilefrine hydrochloride.

Example antiarrhythmic agents include propranol, alprenolol, bufetolol and oxprenolol.

Example vasodilators include oxyfedrine hydrochloride, diltiazem, tolazoline hydrochloride, hexobendine and bamethan sulfate.

Example hypotensive diuretics include hexamethonium bromide, pentolinium, mecamylamine hydrochloride, ecarazine hydrochloride and clonidine.

Example antidiabetics include glymidine sodium, glipizide, fenformin hydrochloride, buformin hydrochloride and metformin.

Example anticoagulants include heparin sodium and sodium citrate.

Example hemolytics include thromboplastin, thrombin, menadione sodium hydrogen sulfite, acetomenaphthone, ε-aminocaproic acid, tranexamic acid, carbazochrome sodium sulfonate and adrenochrome monoaminoguanidine methanesulfonate.

Example antituberculosis agents include isoniazid, ethambutol and p-aminosalicylic acid.

Example hormones include predonizolone, predonizolone sodium phosphate, dexamethasone sodium sulfate, betamethasone sodium phosphate, hexestrol phosphate, hexestrol acetate and methimazole.

Example narcotic antagonists include levallorphan tartrate, nalorphine hydrochloride and naloxone hydrochloride.

Example bone resorption suppressors include (sulfur-containing alkyl)aminomethylenebisphosphonic acid.

Example angiogenesis suppressors include angiogenesis-suppressing steroid [see Science, Vol. 221, p. 719 (1983)], fumagillin (see European Patent Publication No. 325199) and fumagillol derivatives (see European Patent Publication Nos. 357061, 359036, 386667 and 415294).

Of these bioactive substances, water-soluble ones are preferable for application of the present invention, since preparations of water-soluble bioactive substances often show excess initial release.

The water solubility of a bioactive substance is defined as the water-octanol distribution ratio. It is preferable that the present invention be applied to a bioactive substance whose water-octanol solubility ratio is not lower than 0.1, more preferably not lower than 1. Oil-water distribution ratios can be determined by the method described in "Butsuri Kagaku Jikkenho (Physicochemical Experimental Method)", by Jitsusaburo Samejima, published by Shokabo, 1961. Specifically, n-octanol and a buffer of pH 5.5 (1:1 by volume mixture) are placed in a test tube. The buffer is exemplified by Soerenzen buffer [Ergeb. Physiol., 12, 393 (1912)], Clark-Lubs buffer [J. Bact., 2(1), 109, 191 (1917)], MacIlvaine buffer [J. Biol. Chem., 49, 183, (1921)], Michaelis buffer [Die Wasser-stoffionenkonzentration), p. 186 (1914)] and Kolthoff buffer [Biochem. Z., 179, 410 (1926)]. An appropriate amount of such a bioactive substance is placed in the test tube, which is then stoppered and immersed in a constant-temperature chamber (25° C.) with frequent vigorous shaking. When the bioactive substance appears to have dissolved in both liquid phases to reach an equilibrium, the liquid mixture is kept standing or centrifuged; a given amount is pipetted from each of the upper and lower layers, and analyzed for bioactive substance concentration in each layer, to obtain the ratio of the bioactive substance concentration in the n-octanol layer to that in the water layer for the oil-water distribution ratio.

The bioactive substance may be used as such or as a pharmacologically acceptable salt (e.g., salts with inorganic acids such as hydrochloric acid, sulfuric acid and nitric acid, and salts with organic acids such as carbonic acid and succinic acid, when the bioactive substance has a basic group, such as the amino group; salts with inorganic bases such as salts with sodium, potassium and other alkali metals, salts with organic base compounds such as triethylamine and other organic amines, and salts with basic amino acids such as arginine, when the bioactive substance has an acidic group such as the carboxy group).

The content of the bioactive substance such as peptides in sustained-release microcapsules is preferably about 0.01 to 40% (w/w), more preferably about 0.1 to 30% (w/w) of the microcapsule weight, depending on the kind of peptide used, desired pharmacological effect, duration of action and other factors.

A biodegradable polymer is used as the base for the microcapsules of the present invention.

The biodegradable polymer for the present invention preferably has a free carboxyl group at one end. The biodegradable polymer having a free carboxyl group at one end is defined as a biodegradable polymer whose number-average molecular weight, as determined by GPC measurement, and that determined by terminal group quantitation almost agree with each other.

By terminal group quantitation, number-average molecular weight is calculated as follows:

About 1 to 3 g of the biodegradable polymer is dissolved in a mixed solvent of acetone (25 ml) and methanol (5 ml), and the solution is quickly titrated with a 0.05 N alcoholic solution of potassium hydroxide while being stirred at room temperature (20° C.) with phenolphthalein as an indicator to determine the terminal carboxyl group content; the number-average molecular weight is calculated using the following equation:

Number-average molecular weight based on terminal group quantitation=20000×A/B A: Weight mass (g) of the biodegradable polymer B: Amount (ml) of the 0.05 N alcoholic solution of potassium hydroxide added until the titration end point is reached For example, in the case of a polymer having a free carboxyl group at one end, and synthesized from one or more α-hydroxy acids by catalyst-free dehydration polymerization condensation, the number-average molecular weight based on GPC measurement and the number-average molecular weight based on terminal group quantitation almost agree. On the other hand, in the case of a polymer having essentially no free carboxyl group at one end, and synthesized from a cyclic dimer by ring-opening polymerization using a catalyst, the number-average molecular weight based on terminal group quantitation is significantly higher than the number-average molecular weight based on GPC measurement. This difference makes it possible to clearly differentiate a polymer having a free carboxyl group at one end from a polymer having no free carboxyl group at one end.

While the number-average molecular weight based on terminal group quantitation is an absolute value, the number-average molecular weight based on GPC measurement is a relative value that varies depending on various analytical conditions (e.g., kind of mobile phase, kind of column, reference substance, slice width chosen, baseline chosen); it is therefore difficult to have an absolute numerical representation of the latter. However, the fact that the number-average molecular weight based on GPC measurement and that based Qn terminal group quantitation almost agree with each other means that the number-average molecular weight based on terminal group quantitation falls within the range from about 0.4 to 2 times, preferably from about 0.5 to 2 times, and more preferably from about 0.8 to 1.5 times, the number-average molecular weight based on GPC measurement. Also, the fact that the number-average molecular weight based on terminal group quantitation is significantly higher than that based on GPC measurement means that the number-average molecular weight based on terminal group quantitation is about 2 times or more the number-average molecular weight based on GPC measurement.

The weight-average molecular weight of the above-described biodegradable polymer is preferably about 3,000 to 30,000, more preferably about 5,000 to 25,000, and still more preferably about 7,000 to 20,000.

The degree of dispersion of the biodegradable polymer (weight-average molecular weight/number-average molecular weight) is preferably about 1.2 to 4.0, more preferably about 1.5 to 3.5.

Example biodegradable polymers having a free carboxyl group at one end include homopolymers and copolymers synthesized from one or more α-hydroxy acids, usually α-hydroxycarboxylic acid (e.g., glycolic acid, lactic acid, hydroxybutyric acid), hydroxydicarboxylic acids (e.g., malic acid), hydroxytricarboxylic acids (e.g., citric acid) etc. by catalyst-free dehydration polymerization condensation, mixtures thereof, poly-α-cyanoacrylates, polyamino acids (e.g., poly-γ-benzyl-L-glutamic acid) and maleic anhydride copolymers (e.g., styrene-maleic acid copolymers).

Polymerization may be of the random, block or graft type. When the above-mentioned α-hydroxy acids, hydroxydicarboxylic acids and hydroxytricarboxylic acids have an optical active center in their molecular structures, they may be of the D-, L- or DL-configuration.

Biodegradable polymers for the present invention can, for example, be produced by known methods, such as those described in Japanese Patent Unexamined Publication Nos. 17525/1975, 45920/1981(EPA26599), 118512/1982 (EPA52510), 150609/1982(EPA58481), 28521/1986 (EPA172636) and 54760/1987(EPA202065), and European Patent Publication No. 481732, or modifications thereof.

The biodegradable polymer having a free carboxyl group at one end is preferably (1) a lactic acid homopolymer, (2) a lactic acid/glycolic acid copolymer or (3) a biodegradable polymer comprising a mixture of a copolymer of glycolic acid and a hydroxycarboxylic acid represented by the formula (III):

$$\underset{\mathrm{HOCHCOOH}}{\overset{R}{|}} \quad (\mathrm{III})$$

wherein R represents an alkyl group having 2 to 8 carbon atoms (hereinafter referred to as glycolic acid copolymer (A)), and a polylactic acid (hereinafter referred to as polylactic acid (B)).

More preferably, the biodegradable polymer having a free carboxyl group at one end is a lactic acid homopolymer or a lactic acid/glycolic acid copolymer.

When a lactic acid/glycolic acid copolymer or homopolymer is used as the biodegradable polymer, its content ratio (lactic acid/glycolic acid) (mol %) is preferably about 100/0 to 50/50, more preferably about 90/10 to 60/40. The lactic acid/glycolic acid content ratio (mol %) is most preferably about 80/20 to 70/30. A lactic acid homopolymer is also preferred.

The above-described lactic acid homopolymer and lactic acid/glycolic acid copolymer can be produced by a known process, such as that described in Japanese Patent Unexamined Publication No. 28521/1986(EPA172636).

The decomposition/elimination rate of a lactic acid homopolymer varies widely, depending on molecular weight. To obtain a sustained-release preparation of the long acting type (e.g., 1–4 months), it is preferable to use a lactic acid homopolymer whose weight-average molecular weight is within the above-described range.

The decomposition/elimination rate of a lactic acid/ glycolic acid copolymer varies widely, depending on composition or molecular weight. However, drug release duration can be extended by lowering the glycolic acid ratio or increasing the molecular weight, since decomposition/ elimination is usually delayed as the glycolic acid ratio decreases. Conversely, drug release duration can be shortened by increasing the glycolic acid ratio or decreasing the molecular weight. To obtain a sustained-release preparation of the relatively long acting type (e.g., 1 month), it is preferable to use a lactic acid/glycolic acid copolymer whose content ratio and weight-average molecular weight fall in the above ranges. If choosing a lactic acid/glycolic acid copolymer that decomposes more rapidly than that whose content ratio and weight-average molecular weight fall in the above ranges, initial burst is difficult to suppress; if choosing a lactic acid/glycolic acid copolymer that decomposes more slowly than that whose content ratio and weight-average molecular weight fall in the above ranges, it is likely that no effective amount of drug is released during some period.

With respect to the formula (III) above, the linear or branched alkyl group represented by R, which has 2 to 8 carbon atoms, is exemplified by ethyl, propyl, isopropyl, butyl, isobutyl, sec-butyl, tert-butyl, pentyl, isopentyl, neopentyl, tert-pentyl, 1-ethylpropyl, hexyl, isohexyl, 1,1-dimethylbutyl, 2,2-dimethylbutyl, 3,3-dimethylbutyl and 2-ethylbutyl. Preferably, a linear or branched alkyl group having 2 to 5 carbon atoms is used. Such alkyl groups include ethyl, propyl, isopropyl, butyl and isobutyl. More preferably, R is ethyl.

The hydroxycarboxylic acid represented by the formula (III) is exemplified by 2-hydroxybutyric acid, 2-hydroxyvaleric acid, 2-hydroxy-3-methylbutyric acid, 2-hydroxycaproic acid, 2-hydroxyisocaproic acid and 2-hydroxycapric acid, with preference given to 2-hydroxybutyric acid, 2-hydroxyvaleric acid, 2-hydroxy-3-methylbutyric acid and 2-hydroxycaproic acid, with greater preference given to 2-hydroxybutyric acid. Although the hydroxycarboxylic acid may be of the D-, L- or D,L-configuration, it is preferable to use a mixture of the D- and L-configurations wherein the ratio of the D-/L-configuration (mol %) preferably falls within the range from about 75/25 to 25/75, more preferably from about 60/40 to 40/60, and still more preferably from about 55/45 to 45/55.

With respect to glycolic acid copolymer (A), polymerization may be of random, block or graft type. A random copolymer is preferred.

The hydroxycarboxylic acid represented by the formula (III) may be a mixture of one or more kinds in a given ratio.

With respect to the content ratio of glycolic acid and the hydroxycarboxylic acid represented by the formula (III) in glycolic acid copolymer (A), it is preferable that glycolic acid account for about 10 to 75 mol % and hydroxycarboxylic acid for the remaining portion. More preferably, glycolic acid accounts for about 20 to 75 mol %, and still more preferably about 40 to 70 mol %. The weight-average molecular weight of glycolic acid copolymer (A) is normally about 2,000 to 50,000, preferably about 3,000 to 40,000, and more preferably about 8,000 to 30,000. The degree of dispersion of glycolic acid copolymer (A) (weight-average molecular weight/number-average molecular weight) is preferably about 1.2 to 4.0, more preferably about 1.5 to 3.5.

Glycolic acid copolymer (A) above can be produced by a known process, such as that described in Japanese Patent Unexamined Publication No. 28521/1986(EPA172636).

Although polylactic acid (B) may be of the D- or L-configuration or a mixture thereof, it is preferable that the ratio of the D-/L-configuration (mol %) fall within the range from about 75/25 to 20/80. The ratio of the D-/L-configuration (mol %) is more preferably about 60/40 to 25/75, and still more preferably about 55/45 to 25/75. The weight-average molecular weight of polylactic acid (B) is preferably about 1,500 to 30,000, more preferably about 2,000 to 20,000, and still more preferably about 3,000 to 15,000. Also, the degree of dispersion of polylactic acid (B) is preferably about 1.2 to 4.0, more preferably about 1.5 to 3.5.

For producing polylactic acid (B), two methods are known: ring-opening polymerization of lactide, a dimer of lactic acid, and dehydration polymerization condensation of lactic acid. For obtaining polylactic acid (B) of relatively low molecular weight for the present invention, direct dehydration polymerization condensation of lactic acid is preferred. This method is, for example, described in Japanese Patent Unexamined Publication No. 28521/1986 (EPA172636).

Glycolic acid copolymer (A) and polylactic acid (B) are used in a mixture wherein the (A)/(B) ratio (% by weight) falls within the range from about 10/90 to 90/10. The mixing ratio (% by weight) is preferably about 20/80 to 80/20, and more preferably about 30/70 to 70/30. If either component (A) or (B) is in excess, the preparation obtained shows a bioactive substance release pattern no more than that obtained with the use of component (A) or (B) alone; no linear release pattern is expected in the last stage of drug release from the mixed base. Although the decomposition/ elimination rate of glycolic acid copolymer (A) and polylactic acid (B) varies widely, depending on molecular weight or composition, drug release duration can be extended by increasing the molecular weight of polylactic acid (B) or lowering the mixing ratio (A)/(B), since the decomposition/ elimination rate of glycolic acid copolymer (A) is usually higher than that of polylactic acid (B). Conversely, drug release duration can be shortened by decreasing the molecular weight of polylactic acid added or increasing the mixing ratio (A)/(B). Drug release duration can also be adjusted by altering the kind and content ratio of hydroxycarboxylic acid represented by the formula [III].

With respect to sustained-release microcapsules, the content ratio of biodegradable polymer varies, depending on the kind of polymer etc., but is preferably not less than 60% (w/w), more preferably not less than 70% (w/w), relative to the microcapsules.

Especially, in the sustained-release microcapsules of a peptide of the formula (I) as the bioactive substance it is preferred that the bioactive substance is contained at the final content ratio of 5–15% (w/w) based on the final product of the sustained-release microcapsules and the biodegradable polymer is contained at the final content ratio of 80–95% (w/w) based on the same.

Regarding weight-average molecular weight and degree of dispersion, the present specification holds that the former is based on polystyrene obtained by gel permeation chromatography (GPC) with 9 polystyrenes as reference substances with weight-average molecular weights of 120,000, 52,000, 22,000, 9,200, 5,050, 2,950, 1,050, 580 and 162, respectively, and that the latter is calculated therefrom. Measurements were taken using a GPC column KF804L×2 (produced by Showa Denko) and an RI monitor L-3300 (produced by Hitachi, Ltd.), with chloroform as a mobile phase.

The production method of the present invention is hereinafter described in detail.

In the present invention, microcapsules containing a bioactive substance and a biodegradable polymer can, for example be produced from a w/o emulsion with a solution containing a bioactive substance as an internal aqueous phase and a solution containing a biodegradable polymer as an oil phase. Specifically, the known methods of microcapsulation described below, such as the in-water drying method, phase separation method and spray drying method, and modifications thereof are used.

First, a bioactive substance is dissolved or dispersed in water, with a drug support or a drug-retaining substance, such as gelatin, agar, alginic acid, polyvinyl alcohol or a basic amino acid (e.g., Lys, His), dissolved or suspended when necessary, to yield an internal aqueous phase. The drug support is preferably gelatin.

The drug concentration in the internal aqueous phase is preferably 0.1 to 200% (w/v), more preferably 20 to 110% (w/v), and still more preferably 30 to 100% (w/v).

The weight ratio of the drug support and bioactive substance is normally 100:1 to 1:100, preferably 10:1 to 1:50, and more preferably 10:1 to 1:10.

The internal aqueous phase may be supplemented with a pH regulator for retaining bioactive substance stability or solubility, such as carbonic acid, acetic acid, oxalic acid, citric acid, phosphoric acid, hydrochloric acid, sodium hydroxide, arginine, lysine or a salt thereof. In addition, albumin, gelatin, citric acid, sodium ethylenediaminetetraacetate, dextrin, sodium hydrogen sulfite, polyol compounds such as polyethylene glycol, etc., as bioactive substance stabilizers, and commonly used p-oxybenzoates (e.g., methyl paraben, propyl paraben), benzyl alcohol, chlorobutanol, thimerosal etc., as preservatives, may be added.

The internal aqueous phase thus obtained is added to a solution (oil phase) containing a biodegradable polymer, followed by emulsification, to yield a w/o emulsion. Emulsification is achieved by a known dispersing method. Useful dispersing methods include the intermittent shaking method, the method using a mixer, such as a propeller stir-rer or a turbine homomixer, the colloidal mill method, the homogenizer method and the ultrasonication method.

The above-described solution (oil phase) containing a biodegradable polymer is prepared by dissolving the polymer in an organic solvent. Any organic solvent serves this purpose, as long as it has a boiling point not higher than about 120° C., is immiscible with water and dissolves the biodegradable polymer. Such solvents include halogenated hydrocarbons (e.g., dichloromethane, chloroform, chloroethane, trichloroethane, carbon tetrachloride), fatty acid esters (e.g., ethyl acetate, butyl acetate), ethers (e.g., ethyl ether, isopropyl ether) and aromatic hydrocarbons (e.g., benzene, toluene, xylene). These solvents may be used in combination. The organic solvent used is preferably a halogenated hydrocarbon, more preferably dichloromethane.

Although the polymer concentration in the oil phase is not subject to limitation, as long as the final biodegradable polymer content in microcapsules is not less than 60% (w/w), preferably 70 to 99% (w/w), it is preferably about 0.1 to 80% (w/w), more preferably about 1 to 70% (w/w), and most preferably about 10 to 60% (w/w), depending on the molecular weight of said polymer and the kind of solvent.

Next, the thus-obtained w/o emulsion is subjected to a microcapsulation process.

(1) In-water Drying Method

To produce microcapsules from a w/o emulsion by the in-water drying method, for instance, the w/o emulsion is added to another aqueous phase (external aqueous phase), i.e., a third phase, to yield a w/o/w emulsion, after which the solvent is evaporated from the oil phase, to yield microcapsules.

A w/o/w emulsion is prepared by the same emulsification procedure as that used to prepare a w/o emulsion.

Solvent evaporation from the oil phase can be achieved by known methods, including the method in which the solvent is evaporated under normal or gradually reduced pressure during stirring using a propeller stirrer, magnetic stirrer or the like, and the method in which the solvent is evaporated while the degree of vacuum is adjusted using a rotary evaporator or the like.

The volume of the external aqueous phase is normally 1 to about 10,000 times, preferably about 10 to 2,000 times, and more preferably about 50 to 500 times, that of the w/o emulsion prepared.

Before the w/o emulsion is added, the external aqueous phase's temperature may be adjusted to about 10 to 20° C.

An emulsifier may be added to the third, aqueous phase. The emulsifier may be any one, as long as it is capable of forming a stable o/w emulsion. Such emulsifiers include anionic surfactants (e.g., sodium oleate, sodium stearate, sodium lauryl sulfate), nonionic surfactants [e.g., polyoxyethylene sorbitan fatty acid esters (Tween 80, Tween 60, Atlas Powder Company), polyoxyethylene castor oil derivatives (e.g., HCO-60, HCO-50, Nikko Chemicals)], polyvinylpyrrolidone, polyvinyl alcohol, carboxymethyl cellulose, lecithin and gelatin. These emulsifiers may be used singly or in combination. The emulsifier is preferably polyvinyl alcohol. The emulsifier concentration (w/v) can be chosen as appropriate over the range from about 0.01% to 20%, preferably from about 0.05% to 10%, relative to the external aqueous phase.

The thus-obtained microcapsules are centrifuged or filtered to separate them, after which they are washed with distilled water several times to remove the free bioactive substance, drug support, emulsifier etc. adhering to the microcapsule surface. The microcapsules are then again dispersed in distilled water etc. and lyophilized. To prevent mutual aggregation of particles during lyophilization, an anticoagulant [e.g., water-soluble saccharides such as mannitol, lactose, glucose and starches (e.g., corn starch), amino acids such as glycine and alanine, proteins such as gelatin, fibrin and collagen, and inorganic salts such as sodium chloride, sodium bromide and potassium carbonate] may be added. The anticoagulant is preferably mannitol. The mixing ratio (by weight) of microcapsules and anticoagulant is normally about 50:1 to 1:1, preferably about 20:1 to 1:1, and more preferably about 10;1 to 5:1.

(2) Phase Separation Method

For producing microcapsules by the phase separation method, a coacervating agent is gradually added to the above-described w/o emulsion while the emulsion is stirred, to precipitate and solidify the high molecular polymer.

Any coacervating agent can be used, as long as it is a polymeric, mineral oil or vegetable oil compound miscible with the solvent for the high molecular polymer and that does not dissolve the polymer for capsulation. Such coacervating agents include silicon oil, sesame oil, soybean oil, corn oil, cotton seed oil, coconut oil, linseed oil, mineral oil, n-hexane and n-heptane. These may be used in combination of two or more kinds. The thus-obtained microcapsules are filtered to separate them, after which they are repeatedly washed with heptane etc. to remove the coacervating agent. The free drug and solvent are then removed in the same manner as in the aqueous drying method.

(3) Spray Drying Method

For producing microcapsules by the spray drying method, the above-described w/o emulsion is sprayed via a nozzle into the drying chamber of a spray drier to volatilize the organic solvent and water in the fine droplets in a very short time, to yield fine microcapsules. The nozzle is exemplified by the double-fluid nozzle, pressure nozzle and rotary disc nozzle. To prevent microcapsule coagulation or aggregation where desired, an aqueous solution of the above-described anticoagulant may be effectively sprayed via another nozzle, anticoagulant while the w/o emulsion is sprayed.

For production of sustained-release microcapsules of a peptide of the formula (I) as the bioactive substance, preferably, microcapsulation can be conducted by an in-water drying method.

The microcapsules thus obtained may have the water and solvent removed by heating at increased temperature under reduced pressure when necessary.

Microcapsules obtained by the above-described in-water drying method, phase separation method or spray drying method are thermally dried at a temperature not lower than the glass transition point of the biodegradable polymer used as the base at which the particles of said microcapsules do not melt and do not adhere mutually, when necessary, under reduced pressure, to ensure the removal of the water and organic solvent from the microcapsules and improve the sustained-release property. Remaining organic solvent is preferably reduced to such an extent of less than 1000 ppm, preferably less than 500 ppm, most preferably less than 100 ppm.

Glass transition point is defined as the intermediate glass transition point (Tmg) obtained using a differential scanning calorimeter (DSC) when the temperature is increased at a rate of 10 or 20° C. per minute.

Although heating is preferably subsequent to the lyophilization or thermal drying of sustained-release microcapsules, this mode is not limitative; for example, heating may follow microcapsule dispensing.

If the heating temperature is lower than the glass transition point of the biodegradable polymer used as the base, the initial release of the bioactive substance in excess is not improved; if the heating temperature is too high, the risk of microcapsule fusion and deformation, bioactive substance decomposition, deterioration etc. increases. Although heating temperature depends on conditions, it can be determined as appropriate, in consideration of the physical properties (e.g., molecular weight, stability) of the biodegradable polymer used as the base, bioactive substance, mean particle size of microcapsules, heating time, degree of microcapsule drying, heating method etc.

Preferably, microcapsules are thermally dried at a temperature not lower than the glass transition point of the biodegradable polymer used as the base at which the particles of said microcapsules do not melt and do not adhere mutually, more preferably in the temperature ranging from the glass transition point of the biodegradable polymer used as the base to a temperature higher by about 30° C. than the glass transition point. Especially when (1) a lactic acid homopolymer or (2) a lactic acid/glycolic acid copolymer is used, heating temperature is preferably a temperature ranging from the glass transition point of the polymer used to a temperature higher by 5° C. than the glass transition point, more preferably a temperature ranging from the glass transition point of the polymer used to a temperature higher by 3° C.–4° C. than the glass transition point for good sustained release preparation.

Furthermore, it is preferable to heat at a temperature higher by 3° C.–40° C. than the glass transition point in order to avoid and suppress coagulation or aggregation of microcapsules, because such coagulation or aggregation is more likely to occur when heated at a temperature above the temperature higher by 5° C. than the glass transition point, especially at the earlier stage of thermal drying when more organic solvent remains.

Thermal heating time also varies, depending on heating temperature, the amount of microcapsules treated and other factors, it is generally preferable that thermal heating time be about 24 to 120 hours, more preferably about 48 to 96 hours after the microcapsules reach a given temperature. Especially, concerning the upper limit of heating time, to reduce remaining organic solvent and water content below the acceptable level, heating can be continued, while it is preferred to finish thermal drying as soon as the organic solvent and water content is reduced up to the acceptable level, to avoid or minimize physical contact among soften microcapsules and deformation caused by load of piled soften microcapsules.

Any heating method can be used, as long as microcapsules are uniformly heated.

Preferable thermal drying methods include the method in which thermal drying is conducted in a constant-temperature chamber, fluidized bed chamber, mobile phase or kiln, and the method using microwaves for thermal drying, with preference given to the method in which thermal drying is conducted in a constant-temperature chamber.

Although sustained-release microcapsules produced by the method of the present invention can be administered to the living body in the form of fine granules as such, they can also be administered after shaping into various preparations, and can also be used as starting materials to produce such preparations.

Such preparations include injectable preparations, oral preparations (e.g., powders, granules, capsules, tab-lets), nasal preparations and suppositories (e.g., rectal suppositories, vaginal suppositories). Although the amount of bioactive substance in these preparations is variable according to the kind of bioactive substance, dosage form, target disease etc., it is normally about 0.001 mg to 5 g, preferably about 0.01 mg to 2 g, per unit of preparation.

These preparations can be produced by known methods in common use for pharmaceutical making.

For example, sustained-release microcapsules produced by the method of the present invention can be prepared as injectable preparations by suspending in water with a dispersing agent [e.g, Tween 80, HCO60 (produced by Nikko Chemicals), carboxymethyl cellulose, sodium alginate], a preservative (e.g., methyl paraben, propyl paraben, benzyl alcohol, chlorobutanol), an isotonizing agent (e.g., sodium chloride, glycerol, sorbitol, glucose) etc. to yield an aqueous suspension, or by dispersing in a vegetable oil such as olive oil, sesame oil, peanut oil, cottonseed oil or corn oil, propylene glycol, or the like to yield an oily suspension.

Further, sustained-release microcapsules produced by the method of the present invention can be loaded into a chamber of a pre-filled syringe or can be loaded into a chamber together with water with dispersing agents in a separate chamber of the pre-filled syringe, so-called Double-Chamber Pre-filled Syringe.

Furthermore, an injectable preparation of the above-described sustained-release microcapsules may be re-dispersed in the presence of an excipient (e.g., anticoagulants such as mannitol, sorbitol, lactose, glucose), in addition to the above components, then lyophilized or spray dried to solidify them, followed by the addition of distilled water for injection or an appropriate dispersant at use, to yield a more stable sustained-release preparation.

An oral preparation can be produced by, for example, adding an excipient (e.g., lactose, sucrose, starch), a disintegrating agent (e.g., starch, calcium carbonate), a binder (e.g., starch, gum arabic, carboxymethyl cellulose, polyvinylpyrrolidone, hydroxypropyl cellulose) or a lubricant (e.g., talc, magnesium stearate, polyethylene glycol 6000) to sustained-release microcapsules as produced by the method of the present invention, subjecting the mixture to compressive shaping, both by a well-known method, followed by coating to mask the taste or conferring an enteric or sustained-release property by a well-known method when necessary. Useful coating agents include hydroxypropylmethyl cellulose, ethyl cellulose, hydroxymethyl cellulose, hydroxypropyl cellulose, polyoxyethylene glycol, Tween 80, Pluronic F68, cellulose acetate phthalate, hydroxypropylmethyl cellulose phthalate, hydroxypropylmethyl cellulose acetate succinate, Eudragit (Rohm Company, West Germany, methacrylic acid-acrylic acid copolymer), and dyes such as titanium oxide and iron oxide red.

The nasal preparation produced by the method of the present invention in accordance with a well-known method may be solid, semi-solid or liquid. For example, a solid nasal preparation can be produced by powdering the sustained-release microcapsules, as such or in mixture with an excipient (e.g., glucose, mannitol, starch, microcrystalline cellulose), a thickening agent (e.g., natural rubber, cellulose derivative, acrylic acid polymer) etc. A liquid nasal preparation can be produced as an oily or aqueous suspension, in almost the same manner as for an injectable preparation. The semi-solid nasal preparation is preferably an aqueous or oily gel or ointment. All these preparations may contain a pH regulator (e.g., carbonic acid, phosphoric acid, citric acid, hydrochloric acid, sodium hydroxide), an antiseptic (e.g., p-oxybenzoate, chloro-butanol, benzalkonium chloride) etc.

The suppository may be an oily or aqueous solid, semi-solid or liquid prepared by a well-known method from sustained-release microcapsules as produced by the method of the present invention. Any oily base can be used to produce a suppository, as long as it does not dissolve said microcapsules. Such oily bases include glycerides of higher fatty acids [e.g., cacao fat, Witepsol-series products (Dynamite Nobel Company)], moderate fatty acids [e.g., MIGLYOL-series products (Dynamite Nobel Company)], and vegetable oils (e.g., sesame oil, soybean oil, cottonseed oil). Aqueous bases include polyethylene glycols and propylene glycol. Aqueous gel bases include natural rubbers, cellulose derivatives, vinyl polymers and acrylic acid polymers.

Sustained-release microcapsules produced by the method of the present invention are preferably used in the form of an injectable preparation.

When sustained-release microcapsules produced by the method of the present invention are used in the form of an injectable suspension, for instance, their mean particle size is chosen over the range from about 0.1 to 500 $\mu$m, as long as the requirements concerning the degree of dispersion and needle passage are met. Preferably, the mean particle size is about 1 to 300 $\mu$m, more preferably about 2 to 200 $\mu$m.

The sustained-release microcapsules produced by the method of the present invention are capable of releasing a bioactive substance for a prolonged period ranging from a few days to about 1 year and thus can be administered with an administration schedule of once a few days or a week to even once a year, usually once a month to once per a few months.

The sustained-release microcapsule preparation produced by the method of the present invention is of low toxicity and can be used safely.

Although varying widely depending on kind and content of active ingredient bioactive substance, dosage form, duration of drug release, subject animal species (e.g., warm-blooded mammals such as mice, rats, horses, bovines and humans), target disease (e.g., sex hormone-dependent diseases such as prostatic cancer, prostatic hypertrophy, endometriosis, dysmenorrhea, precocious puberty and breast cancer, and contraception) and other factors, the dose of the sustained-release microcapsule preparation produced by the method of the present invention may be set at any level, as long as the active ingredient is effective. The dose of the preparation per administration can be chosen as appropriate over the range from about 1 mg to 10 g, preferably from about 5 mg to 2 g per adult (weight 50 kg). When the sustained-release preparation is used as an injectable suspension, its volume can be chosen as appropriate over the range from about 0.1 to 5 ml, preferably from about 0.5 to 3 ml.

Peptide (I) or (II) or salts thereof for the present invention possess LH-RH agonizing or antagonizing activity; sustained-release microcapsule preparations containing peptide (I) or (II) and salts thereof, produced by the production method of the present invention, are useful as agents treating sex hormone dependent diseases such as prostatic hypertrophy, prostatic cancer, hysteromyoma, endometriosis, dysmenorrhea, precocious puberty and breast cancer, and as contraceptives. Especially when peptide (I) or a salt thereof is used as the bioactive agent for the agents treating the above-mentioned diseases or contraceptives, unit dose for an adult (weighting 50 kg) of peptide (I) per se ranges from 1 mg to 100 mg, preferably 2 mg to 50 mg.

EXAMPLES

The present invention is hereinafter described in more detail by means of the following examples.

In the description below, Tmg represents an intermediate glass transition point as defined above.

Example 1

One gram of leuprorelin acetate (TAP-144) and 157.5 mg of gelatin were dissolved in 1.0 ml of distilled water, previously heated to 70–80° C., with heating. To this solution, while being slightly warmed to the extent that the gelatin did not solidify, 21 g of a solution of 7.85 g of lactic acid/glycolic acid copolymer (lactic acid/glycolic acid=75/25 mol %, viscosity 0.155, weight-average molecular weight about 11,000, these viscosity and weight-average molecular weight were determined in the manner mentioned below, Wako Pure Chemical) in 13.15 g of dichloromethane was added, followed by stirring emulsification with a small homogenizer for several minutes, to yield a w/o emulsion. After being cooled to 10–20° C., this emulsion was injected to 5,000 ml of a 0.1% (w/v) aqueous solution of polyvinyl alcohol, previously adjusted to 10–20° C., followed by stirring emulsification with a turbine type homomixer, to yield a w/o/w emulsion. This emulsion was stirred at 20–35° C. to volatilize the dichloromethane and solidify the internal w/o emulsion, which was then collected using a centrifuge. The collected solid was again dispersed in distilled water and centrifuged, after which the free drug, polyvinyl alcohol etc. were washed down. The collected microcapsules were suspended in a small amount of distilled water, in which 1.5 g of D-mannitol was dissolved; the resulting microcapsule suspension was lyophilized under reduced pressure to yield microcapsules.

Weight-Average Molecular Weight:

Dissolve 0.20 g of the copolymer in 10 ml of tetrahydrofuran (THF) and use this solution as the sample solution. Separately, dissolve 0.1 g of each of standard polystyrene preparations [Toso (Japan), Catalog No. F-10, F-2, A-5000 and A-1000, having weight-average molecular weights of about 96400, about 5570, about 19600 and about 820, respectively were used], in 10 ml of THF, and use this solution as standard solution A. Also, dissolve 0.1 g of each of other standard polystyrene preparations [Toso (Japan) Catalog No. F-4, F-1, A-2500 and A-500 having weight-average molecular weights of about 37900, about 9100, about 2980 and about 500, respectively were used], in 10 ml of THF, and use this solution as standard solution B. Analyze 100 μl of each of the sample solution and standard solutions A and B by gel permeation chromatography under the operating conditions shown below, and determine weight-average molecular weight ($M_W$) as directed below:

(Operating Conditions)

Detector: RI detector (Shodex RI SE-51, Showa Denko) or equivalent

Columns: Connect pre-column Shodex A-800p (50×6 mm i.d.) with Shimadzu HSG-30 (500×7.9 mm i.d.), Shimadzu HSG-20 (500×7.9 mm i.d.), Shimadzu HSG-15 (500×7.9 mm i.d.) and Shimadzu HSG-10 (500×7.9 mm i.d.) in descending order of packing pore size, or equivalent.

Column temperature: Constant around 50° C.

Mobile phase: Tetrahydrofuran

Flow rate 1.0 ml/min

Injection volume: 100 μl (Calculation) Plot retention times for standard polystyrene solutions A and B versus logarithmic molecular weight to draw working calibration curves. Next, fractionate the copolymer components eluted from the sample solution at 30-second intervals, and determine the area of each fraction by the automatic area integration method.

Viscosity: Weigh precisely about 1.0 g of the copolymer, dissolve in chloroform to make exactly 100 ml, and use this solution as the sample solution. Measure fall time with the sample solution and chloroform by viscometry at 25° C. using Ubbelohde's viscometer, and determine viscosity in accordance with the following formula $$\text{Viscosity} = \frac{\log_e\left[\frac{\text{sample solution fall time (sec)}}{\text{chloroform fall time (sec)}}\right]}{\text{sample weight (g)}}$$

Example 2

Using lactic acid/glycolic acid copolymer (lactic acid/glycolic acid=75/25, viscosity 0.154, weight-average molecular weight about 10300, viscosity and weight-average molecular weight were determined in the same manner as described in Example 1) instead of the copolymer used in Example 1, microcapsules were produced in the same manner as Example 1.

Example 3

Using lactic acid/glycolic acid copolymer (lactic acid/glycolic acid=75/25, viscosity 0.155, weight-average molecular weight about 11500, viscosity and weight-average molecular weight were determined in the same manner as described in Example 1) instead of the copolymer used in Example 1, microcapsules were produced in the same manner as Example 1.

Example 4

Microcapsules as obtained in Example 1 were thermally dried at 50° C., higher by 3° C. than the Tmg (° C.) of the base lactic acid/glycolic acid copolymer, under reduced pressure for about 24 hours to yield a powdery sustained-release microcapsule preparation.

Example 5

Microcapsules as obtained in Example 1 were thermally dried at 50° C., higher by 3° C. than the Tmg (° C.) of the base lactic acid/glycolic acid copolymer, under reduced pressure for about 48 hours to yield a powdery sustained-release microcapsule preparation.

Example 6

Microcapsules as obtained in Example 1 were thermally dried at 50° C., higher by 3° C. than the Tmg (° C.) of the base lactic acid/glycolic acid copolymer, under reduced pressure for about 96 hours to yield a powdery sustained-release microcapsule preparation.

Example 7

Microcapsules as obtained in Example 1 were thermally dried at 50° C., higher by 3° C. than the Tmg (° C.) of the base lactic acid/glycolic acid copolymer, under reduced pressure for about 120 hours to yield a powdery sustained-release microcapsule preparation.

According to the production method of the present invention, it is possible to provide sustained-release microcapsules possessing pharmaceutical characteristics clinically very favorable in that a bioactive substance is released at constant rate over a very long period of time ranging from a few days to a year, usually from one week to a few months, from just after administration with dramatically suppressed initial release of the bioactive substance in excess (e.g. 50%) just after administration and with minimum retention of organic solvent.

Japanese Patent Application No. 226,457/1995 filed Sep. 4, 1995, which is the priority document of the present application, is hereby incorporated by reference in its entirety.

Gly-NH-$R_6$ ($R_6$ represents a hydrogen atom or a lower alkyl group with or without a hydroxyl group) or NH-$R_6$ ($R_6$ has the same definition as that shown above); or a salt thereof.

5. A method for production of claim 1, wherein said bioactive substance is: (Pyr)Glu-His-Trp-Ser-Tyr-D-Leu-Leu-Arg-Pro-NHCH$_2$-CH$_3$ or a salt thereof.

6. A method for production of claim 1, wherein said bioactive substance is a peptide represented by the formula (II):

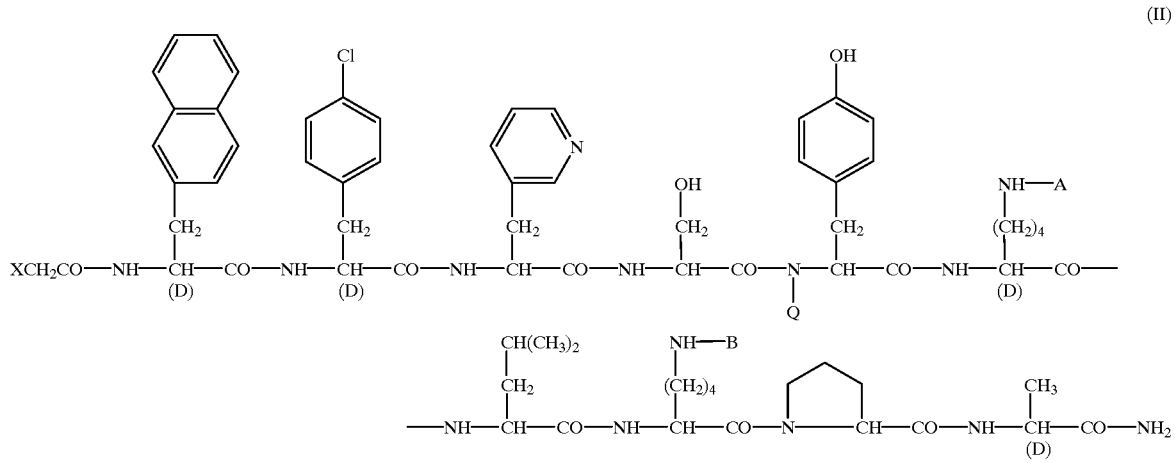

We claim:

1. A method of production of sustained-release microcapsules that comprises obtaining microcapsules comprising a bioactive substance that is encapsulated with a homopolymer or copolymer of lactic acid/glycolic acid having a lactic acid/glycolic acid ratio of 100/0 to 50/50 mol %, and thermally drying the obtained microcapsules at a temperature ranging from the glass transition point of said homopolymer or copolymer of lactic acid/glycolic acid to a temperature up to 5° C. higher than the glass transition point of the homopolymer or copolymer of lactic acid/glycolic acid for about 24 to about 120 hours to produce the sustained-release microcapsules comprising, relative to the weight of the sustained-release microcapsule, not less than 60% by weight of the homopolymer or copolymer of lactic acid/glycolic acid based on the weight of the microcapsule.

2. A method for production of claim 1, wherein said bioactive substance is a peptide having a molecular weight of about 200 to 20,000.

3. A method for production of claim 1, wherein said bioactive substance is luteinizing hormone-releasing hormone or an analog thereof.

4. A method for production of claim 1, wherein said bioactive substance is a peptide represented by the formula (I):

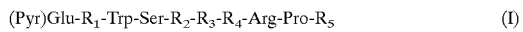

wherein $R_1$ represents His, Tyr, Trp or p-NH$_2$-Phe; $R_2$ represents Tyr or Phe; $R_3$ represents Gly or a D type amino acid residue; $R_4$ represents Leu, Ile or Nle; and $R_5$ represents wherein X represents a hydrogen atom or a tetrahydrofurylcarboxamido; Q represents a hydrogen atom or methyl; A represents nicotinoyl or N,N'-diethylamidino; and B represents isopropyl or N,N'-diethylamidino or a salt thereof.

7. A method for production of claim 6, wherein X is a tetrahydrofurylcarboxamido.

8. A method for production of claim 6, wherein X is (2S)-tetrahydrofurylcarboxamido.

9. A method for production of claim 6, wherein X is (2S)-tetrahydrofurylcarboxamido, Q is methyl, A is nicotinoyl, and B is isopropyl.

10. A method for production of claim 1, wherein said bioactive substance is thyroid horomone-releasing hormone.

11. A method for production of claim 1, wherein the content ratio of said homopolymer or copolymer of lactic acid/glycolic acid is not less than 70% (w/w).

12. A method for production of claim 1, wherein the weight-average molecular weight of said biodegradable polymer is 3,000 to 30,000.

13. A method for production of claim 1, wherein microcapsules are thermally dried for about 48 to 120 hours.

14. A method for production of claim 1, wherein the microcapsules are obtained by an in-water drying method.

15. A method for production of claim 1, wherein the content ratio of the bioactive substance relative to the sustained-release microcapsules is 0.01 to 40% (w/w).

16. A method for production of claim 4, wherein the sustained-release microcapsules contain the bioactive substance at the final content ratio of 5–15% (w/w) and the homopolymer or copolymer of lactic acid/glycolic acid at the final content ratio of 85–95% (w/w).

* * * * *